(12) United States Patent
Jude et al.

(10) Patent No.: US 8,784,746 B2
(45) Date of Patent: Jul. 22, 2014

(54) SYSTEMS, COMPONENTS, AND METHODS FOR STERILIZING MEDICAL WASTE

(71) Applicants: Peter A. Jude, Maple Lake, MN (US); Stephen E. Pellegrene, Plymouth, MN (US); Michael J. Hofer, Fargo, ND (US)

(72) Inventors: Peter A. Jude, Maple Lake, MN (US); Stephen E. Pellegrene, Plymouth, MN (US); Michael J. Hofer, Fargo, ND (US)

(*) Notice: Subject to any disclaimer, the term of this patent is extended or adjusted under 35 U.S.C. 154(b) by 0 days.

(21) Appl. No.: 13/970,830

(22) Filed: Aug. 20, 2013

(65) Prior Publication Data

US 2013/0341444 A1 Dec. 26, 2013

Related U.S. Application Data

(63) Continuation of application No. 13/681,131, filed on Nov. 19, 2012, now Pat. No. 8,518,339.

(60) Provisional application No. 61/580,000, filed on Dec. 23, 2011.

(51) Int. Cl.
  *A61L 2/20* (2006.01)
  *B09B 3/00* (2006.01)
  *A61L 11/00* (2006.01)
  *B02C 19/00* (2006.01)

(52) U.S. Cl.
  CPC ............... *A61L 2/202* (2013.01); *B09B 3/0075* (2013.01); *A61L 2/20* (2013.01); *A61L 11/00* (2013.01); *Y10S 241/606* (2013.01); *B09B 3/00* (2013.01); *B02C 19/0075* (2013.01)
  USPC .............. 422/292; 241/60; 241/606; 210/173

(58) Field of Classification Search
  CPC ........................................................ A61L 2/20
  USPC ....................... 422/292; 210/173; 241/60, 606
  See application file for complete search history.

(56) References Cited

U.S. PATENT DOCUMENTS

| 4,578,185 | A | 3/1986 | Wilson |
|---|---|---|---|
| 5,078,965 | A | 1/1992 | Pearson |
| 5,116,574 | A | 5/1992 | Pearson |
| 5,591,117 | A | 1/1997 | Zelno |
| 5,820,541 | A | 10/1998 | Berlanga |

(Continued)

OTHER PUBLICATIONS

European Patent Office—International Searching Authority, Invitation to Pay Additional Fees and Communication Relating to the Results of the Partial International Search for PCT/US2012/071266, 6 pages, Apr. 26, 2013.

*Primary Examiner* — Sean E Conley
(74) *Attorney, Agent, or Firm* — Fantastic IP Consulting; Eduardo E. Drake (57) ABSTRACT

To improve throughput of biomedical waste treatment, the present inventors devised an exemplary ozone-based system including a shredder, a roll-off treatment bin with ozone injectors, an ozone source, and a controller. The controller monitors electric current drawn by the shredder as shredded waste enters the ozone-enriched treatment bin. In response to current falling below a predetermined low level, indicating that a batch of waste has been shredded and loaded into the treatment bin, the controller starts a treatment timer. The timer measures elapsed ozone treatment or exposure time. If additional waste is added to the shredder and a subsequent low-current condition is detected, the controller restarts the treatment timer. Expiration of the timer indicates that the waste in the roll-off bin is sterilized and ready for transport to landfills. The exemplary system provides continuous waste processing and promises to boost throughput by 50% over some conventional ozone-based waste-treatment systems.

19 Claims, 4 Drawing Sheets

(56) References Cited

U.S. PATENT DOCUMENTS

| | | |
|---|---|---|
| 6,387,241 B1 | 5/2002 | Murphy |
| 6,446,887 B1 | 9/2002 | Swisher |
| 6,494,391 B2 | 12/2002 | Mosenson |
| 7,550,111 B2 | 6/2009 | Klaptchuk |
| 8,100,989 B2 | 1/2012 | Kunik |
| 8,163,045 B2 | 4/2012 | Kunik |
| 8,425,857 B2 * | 4/2013 | Glazer et al. .................. 422/292 |
| 2008/0159910 A1 * | 7/2008 | Dick et al. ...................... 422/40 |
| 2009/0123339 A1 | 5/2009 | Sampson |
| 2012/0060705 A1 | 3/2012 | Kaptein |

* cited by examiner

SYSTEMS, COMPONENTS, AND METHODS FOR STERILIZING MEDICAL WASTE

RELATED APPLICATIONS

This application is a continuation of allowed U.S. patent application Ser. No. 13/681,131 which was filed on Nov. 19, 2012 and which claims priority to U.S. Provisional Patent Application 61/580,000, which was filed on Dec. 23, 2011. The disclosures of both applications are incorporated herein by reference in their entirety.

COPYRIGHT NOTICE AND PERMISSION

A portion of this patent document contains material subject to copyright protection. The copyright owner has no objection to the facsimile reproduction by anyone of the patent document or the patent disclosure, as it appears in the Patent and Trademark Office patent files or records, but otherwise reserves all copyrights whatsoever. The following notice applies to this document: Copyright© 2011, Peter A. Jude, Stephen E. Pellegrene, and Michael J. Hofer.

TECHNICAL FIELD

Various embodiments of the invention concern medical waste treatment, particularly systems and methods using ozone gas.

BACKGROUND

One of the most important concerns of public health systems across the world is controlling or reducing the spread of infectious diseases. This concern is particularly acute in hospitals and other medical care and testing facilities where ill patients come into contact with caregivers, other patients, and visitors. These facilities employ elaborate measures to reduce this risk, including not only mandatory hand-washing and frequent sanitization of equipment, furniture, walls, and floors, but also use of disposable products, such as syringes and hypodermic needles, gloves, bandages, etc. Additionally, great care is taken in disposing of medical waste, particularly biomedical waste.

Biomedical waste includes blood and blood products, tissues removed during surgery and disposable items used and discarded in the normal course of surgical and other medical procedures. Many cities and states mandate special processing of biomedical waste, typically by incineration, autoclaving, or chemical sterilization, to destroy disease-causing pathogens before allowing the waste into local landfills. However, incineration and autoclaving are expensive in terms of their energy usage and affect on local air quality, and chemical sterilizers are typically toxic, posing additional risks to waste-management workers and the environment.

In response to these shortcomings, some waste-treatment processors have built systems that sterilize waste using ozone gas, a form of oxygen that reverts to natural oxygen after performing its sterilization function. For example, U.S. Pat. No. 7,550,111 describes a vertically oriented machine that drops biomedical waste from a top-mounted hopper through a shredder into an ozone-treatment chamber. The chamber holds and exposes the shredded waste to ozone for a period of time, such as 15 minutes, before conveying into a collection bin for later transport to a landfill.

One problem that the present inventors recognized with this system is that its waste-processing speed (throughput) is less than desirable for some medical facilities. The low throughput can result in prolonged storage of unsterilized waste as it awaits processing, exposing staff and patients not only to unpleasant odors, but also to a risk of infection.

Accordingly, the present inventors identified a need for better ozone-based biomedical waste processing systems.

SUMMARY

To address this and/or other needs, the present inventors devised, among other things, exemplary systems, methods, and related components for processing biomedical waste and non-hazardous pharmaceuticals using ozone. One exemplary system, which allows for continuous processing of waste, includes a shredder, a detachable roll-off treatment bin, an ozone source, and a controller. The controller monitors electrical activity of the shredder, for example electrical current, as shredded waste enters the ozone-enriched treatment bin. In response to electric current falling below a predetermined low-level (indicative of the shredder being finished or nearly finished shredding a hopper load of medical waste, the controller starts a treatment timer, for example a 60-minute timer. The timer, which runs as shredded waste is being exposed to sterilizing ozone in the treatment bin, is reset or restarted each time the controller senses a change in the operating state of the shredder. If additional waste is added to the shredder and a subsequent low-load condition is detected, the controller restarts the treatment timer.

Normal operation of the exemplary system yields a treatment bin containing waste at various levels of sterilization as the bin, or container, is filled. For example, after the system has been operating continuously to process waste for a time equal to 1.5 treatment periods, the bin will contain a portion of waste that is sterilized and a portion of waste (added after the first treatment period) that is not fully sterilized.

Unlike some prior ozone-based waste treatment systems, this exemplary system provides continuous processing of medical waste, without the intermediate ozone—dwell stage prior to conveying the waste into the treatment bin, thereby improving throughput by 50% or more according to some estimates.

DETAILED DESCRIPTION OF EXEMPLARY EMBODIMENTS

This document, which includes the referenced drawings and appended claims, describes one or more specific embodiments of one or more inventions. These embodiments, offered not to limit but only to exemplify and teach the invention(s), are shown and described in sufficient detail to enable those skilled in the art to implement or practice the inventions. Thus, where appropriate to avoid obscuring the invention, the description may omit certain information known to those of skill in the art.

This document may use relational terms, such as second, top and bottom, and the like. These terms may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to be open ended, such that a process, method, article, or apparatus that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without further constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

Exemplary Systems

Figure 1:
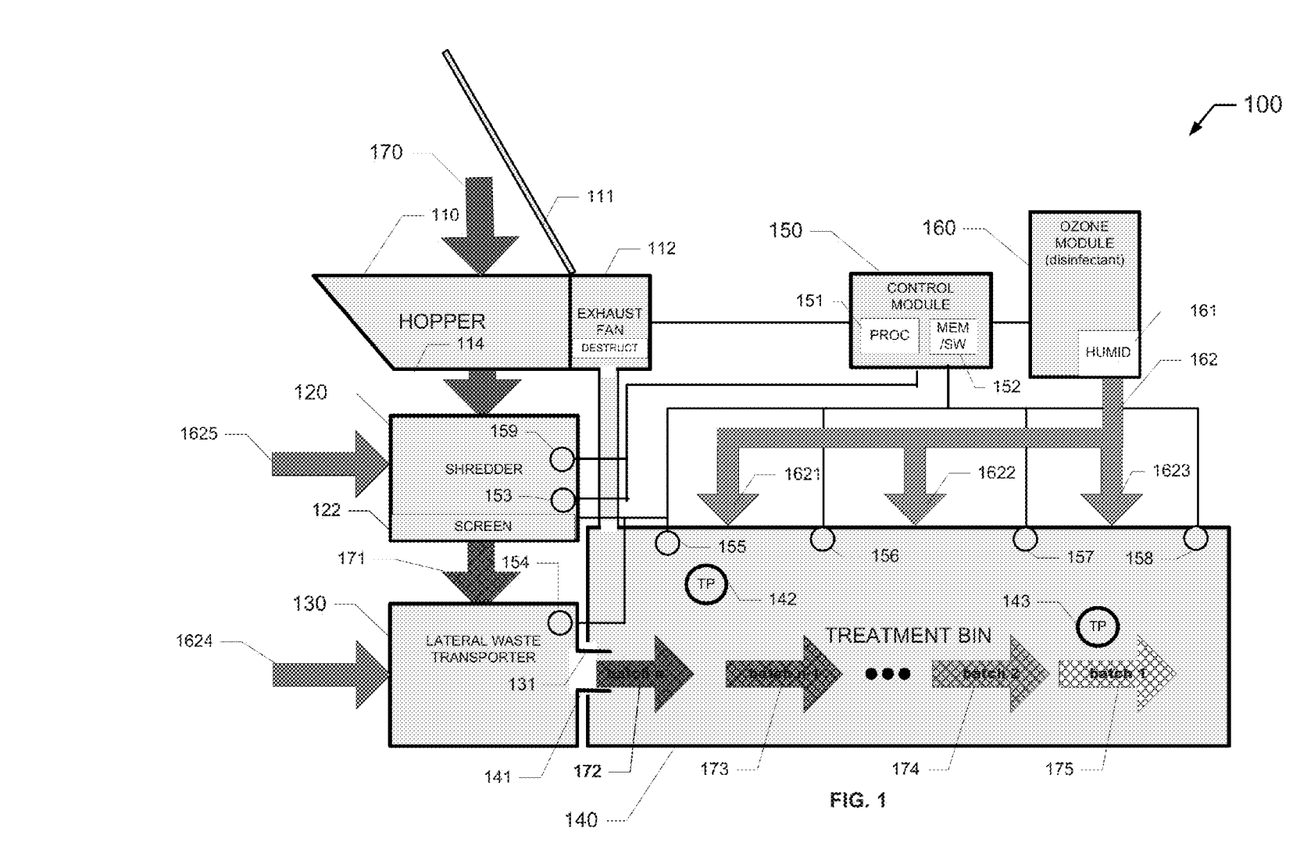
FIG. 1 is a schematic diagram of an exemplary waste treatment system 100 which corresponds to one or more embodiments of the present invention.

FIG. 1 shows an exemplary medical waste treatment system 100. System 100 includes a hopper 110, a shredder 120, a lateral waste transporter 130, a roll-off treatment bin (or container) 140, a control module 150, and an ozone module 160.

Hopper 110 receives biomedical waste for processing. In the exemplar embodiment, the hopper has a capacity of 33.25 cubic feet of material. In some embodiments, an electromechanical or hydraulic lift (not shown in this figure) raises and dumps waste container into the hopper. Hopper 110 includes a lid 111 and an exhaust fan 112 for exhausting waste gases and odors from the hopper. In the exemplary embodiment, exhaust fan 112 also includes an ozone destruct system, such as the ODS-50H 50-SCFM unit from Ozone Water Systems of Phoenix, Ariz., for converting ozone gas back to oxygen. It also includes a bottom opening 114 which allows waste to fall under the weight of gravity onto shredder 120.

Shredder 120, which is positioned underneath hopper 110, receives waste from hopper 110. In the exemplary embodiment, shredder 120 includes a 4-shaft shredder and a lower opening covered by a screen 122. Exemplary shredders include SSI Shredder Systems Model Q55ED Shredder or Q70ED (36"×31" or 44"×40" cutting chamber) to shred the material by up to 90%. The exemplary screen includes openings of approximately 0.75-2.0 inches in diameter or maximal width for non-circular geometries which restricts the maximal size of the waste particles allowed to enter lateral waste transporter 130.

Lateral waste transporter 130, which is positioned or stacked underneath shredder 120, receives shredded waste and transports it laterally through a right-cylindrical extension nozzle 131 into opening 141 of treatment bin 140. In the exemplary embodiment, lateral waste transporter includes an auger, a conveyor belt, plunger, and/or blower. Some embodiments may combine the shredder and auger into a single machine. The exemplary embodiment uses a Sani-Tech System ST1546/36-15HP Refuse & Recycling Compactor.

Treatment bin 140, which may take various forms such as a 10-, 15-, 20-, 30-, or 40-cubic yard rectangular or octagonal steel roll-off container or dumpster, includes test ports 142 and 143. Test ports 142 and 143 are used for accessing and testing the sterilization status of waste within the treatment bin. As shown below in other embodiments, the treatment bin includes a disinfectant distribution system. Some embodiments also include an exhaust manifold within the treatment bin, for example, a central perforated pipe mounted to the ceiling of the bin and in fluid communication with exhaust fan 112.

Control module 150 includes a processor 151, a memory 152, and sensors 153-159. Processor 151 includes one or more processing or control circuits, which provide control signals to various valves and safety interlocks (not shown) in accord with machine-readable and executable instructions and control parameters stored in memory 152. For example, in the exemplary embodiment control module 150 includes a resettable and programmable dwell timer implemented in software, hardware, or firmware. (In some embodiments, processor 151 takes the form of a programmable logic controller.) Sensors 153-158, which include ozone (or more generally disinfectant) sensors, such as Teledyne M465 Ozone Monitor probes, are positioned at various points in system 100 to allow for monitoring and control of ozone distribution. Specifically, sensor 153 is positioned on or within shredder 120; sensor 154 is positioned on or within lateral waste transporter 130; and sensors 155-158 are distributed across a top region of treatment bin 140. Sensor 159, positioned on shredder 120 or associated electrical circuitry, provides shredder operational or load status information to control module 150. A variety of sensors may be used, including, for example, self-calibrating current sensing switches coupled to sense electrical current drawn by the shredder. Control module 150 also controls ozone module 160.

Ozone module or generator 160, which includes a humidifier 161 for humidifying ozone gas, is in fluid communication with ozone injectors 1621-1625. Moisture-saturated ozone gas has much higher oxidation potential than dry gas, enhancing sterilization efficacy of the ozone and reducing flammability. In some embodiments, injectors 1621-1625 are electrically controlled valves coupled to control module 150. Injectors 1621-1625 are positioned along a top region of treatment bin 140. (Some embodiments position these injectors along a bottom portion of the treatment bin.) Injectors 1624 and 1625 are positioned respectively on or within shredder 120 and lateral waste transporter 130, allowing for selective injection of ozone or humidified ozone into the shredder and transporter, for example to sterilize the shredder and transporter prior to maintenance or in some instances to provide a first-stage or low-level sterilization for odor control. (In some embodiments, ozone module 160 also includes a pressurized air (or other non-ozone gas) tank for use in selectively forcing high-pressure gas out of injectors 1621-1625 to clear away shredded waste that may interfere with the desired dispersion of ozone throughout the treatment bin.)

In the case of first-stage sterilization, the waste transport time through the transporter may be increased to allow for partial sterilization of the biomedical waste. For example, the transit time may be increased (or transit rate decreased) to allow for 45- or 60-second ozone exposure at a higher, lower, or similar ozone concentration than in the treatment bin. In some embodiments, the ozone concentration may be substantially greater in the shredder and/or transporter than in the treatment bin, for example 10,000-15,000 PPM as compared to 3,000-7,000 PPM, to obtain a faster sterilization rate during the first stage than during the second stage.

In general operation, a batch of waste material 170 is fed through hopper 110 onto shredder 120, where it is shredded and screened, falling under its own weight into lateral transporter 130 and denoted as batch 171 in FIG. 1. Transporter 130 laterally conveys shredded waste batch 172 into treatment bin 140, where it dwells for at least a minimum prescribed amount of time to ensure its sterilization. The prescribed dwell time, for example, 45, 50, 55, or 60 minutes, is contingent on the type and density of the waste as well as the ozone concentration and humidity level in the treatment bin. (In embodiments that provide higher ozone concentrations in the shredder and/or transporter than in the treatment bin, the dwell or treatment time in the treatment bin may be significantly lower than in the embodiments without a higher first-stage ozone concentration.)

Notably, the shredder and transporter operate continuously, that is without stoppage, as long as waste is available in the hopper and the shredder is shredding, providing successive batches of shredded waste to the treatment bin. In some embodiments, the hopper is large enough to hold two or more waste bins or receptacles of waste.

In the exemplary embodiment, the dwell or treatment time is controlled by the control module, which includes a treatment bin timer, or dwell timer. The timer is set and selectively reset by the controller based on activity of the auger or shredder in some embodiments, specifically the electrical current load on the auger or shredder as sensed by sensor 159. More specifically, the exemplary system starts the timer with the initial start of the auger and every time the auger is stopped and restarted, ensuring that the last batch of waste material is left in the treatment bin for at least the full duration of the treatment timer. Batches of waste prior to the last batch to enter the treatment bin are subject to longer periods of treatment. In ordinary operation, the exemplary system prevents decoupling of the treatment bin while the treatment timer is still counting down (or up as the case may be in some embodiments.)

FIG. 1 shows that as a result of operation, treatment bin 140 will contain shredded batches of biomedical waste at various levels of sterilization, specifically batches 173-175. In some cases, each batch will correspond approximately to the waste volume or weight of a single waste bin or receptacle, or more generally of the hopper. Moreover, each batch will have absorbed a different level of ozone and thus be at different sterilization level (stages).

Estimates are that a batch will be fully sterilized at least after an hour (60 minutes), within the treatment bin, assuming appropriate levels of ozone concentration during that time, for example 7000 ppm. The actual minimum treatment time to achieve full sterilization will be contingent on the exact nature and density of waste and specific treatment conditions (temperature, humidity, waste granularity, ozone concentration, for example). However, given the variance of the waste nature and density, and a desire for 100% sterilization, a minimum time that includes an appropriate safety margin is desirable. One hour is believed to be one such treatment time period, however, further testing may reveal that 45, 30, 20, 10, or even 5 minutes may be possible for certain ozone-humidity levels.

In the illustration, batch 172 is assumed to be the latest or most recent batch added to bin 140 and batches 173-75 are batches that were added previously, with the time between the start of each batch being a function of the waste loading, shredding, and transport rates, for example 5 minutes. Batch 175 is shown in white to represent that it is fully sterilized after being in the treatment bin for at least a prescribed minimum time, such as 60 minutes. Batch 174 is shown in light gray to represent that it is not fully sterilized and has been in the treatment bin for a time period less than the prescribed minimum time, for example, a period of 55 minutes. Batch 173 is shown in dark gray to represent that it is also not fully sterilized after being in the treatment bin a time period less than each of the prior batches, batches 174 and 175 for example.

Figure 2:
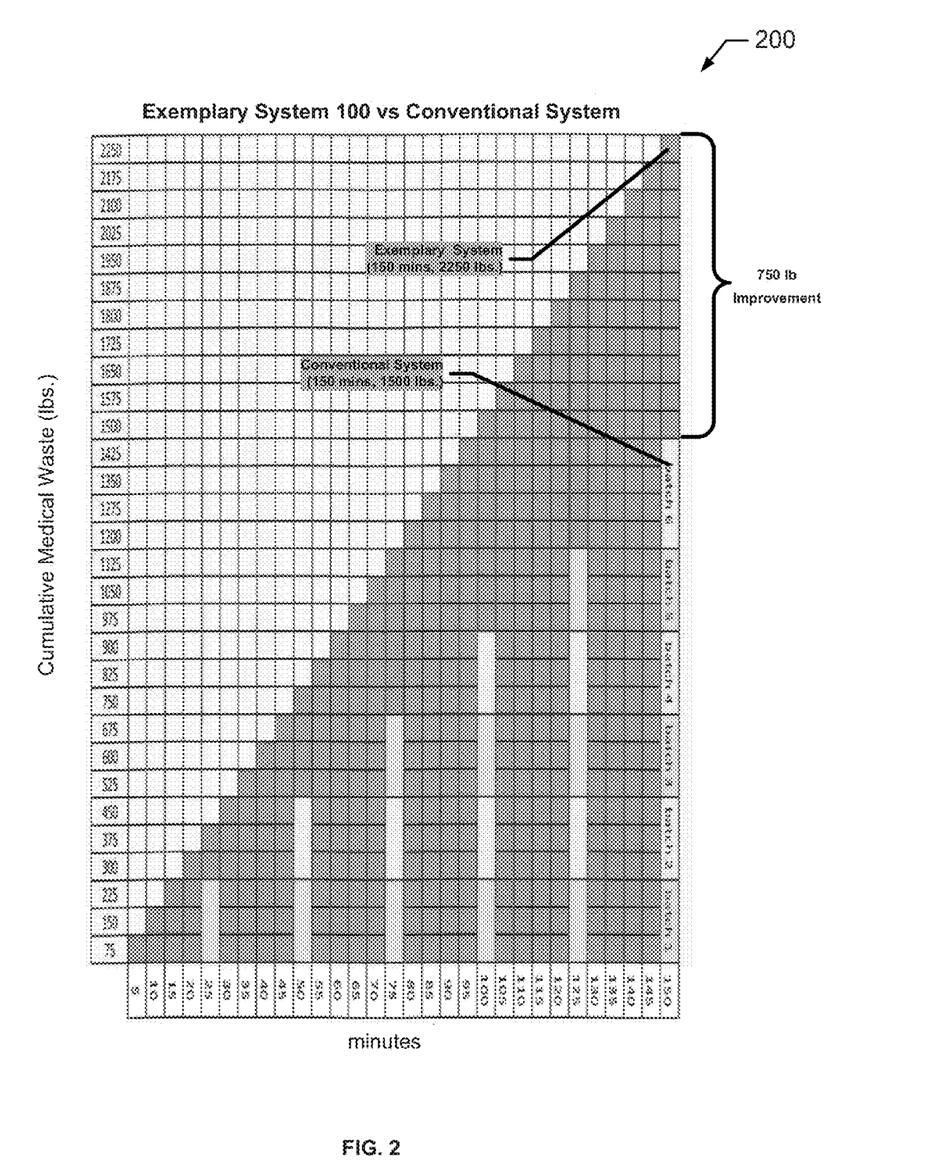
FIG. 2 is a graph which illustrates projected performance of system 100 relative to a conventional waste-treatment system and which corresponds to one or more embodiments of the present invention.

FIG. 2 shows a graph of estimated performance of a continuous inline processing of medical waste according to the method of the exemplary embodiment relative to a conventional method taught in U.S. Pat. No. 7,550,111. The estimated performance of system 100 assumes use of a 36×31 inch cutting chamber 4-shaft shredder. The graph shows that exemplary system 100 provides a 50% improvement, demonstrating the powerful throughput advantage of the relocating or collocating sterilization treatment in the dumpster or waste treatment bin and operating the system continuously, as opposed to the using an intermediate treatment chamber in the stop-and-start manner reported in the '111 patent.

Figure 3A:
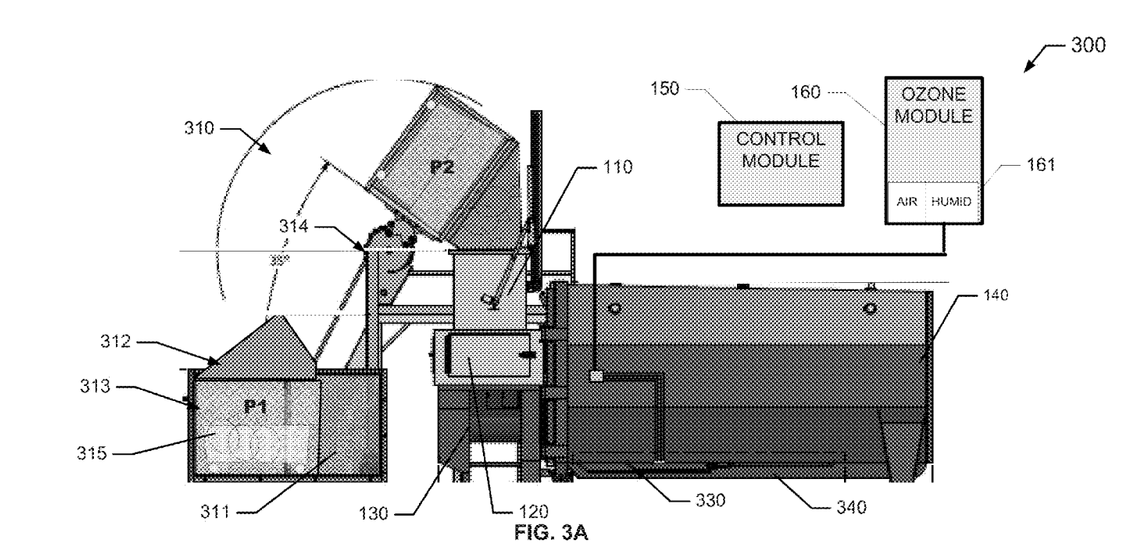
FIGS. 3A-3C are views of an exemplary waste treatment system 300, which is similar in some respects to system 100 and which corresponds to one or more embodiments of the present invention.
Figure 3B:
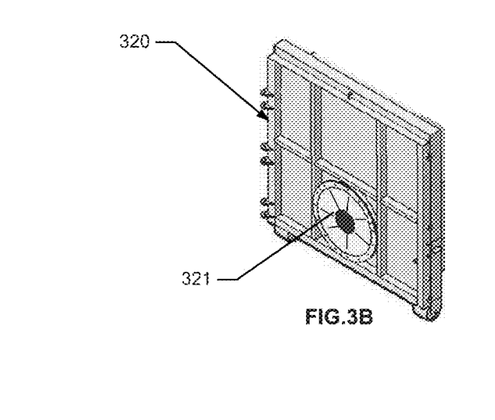
Figure 3C:
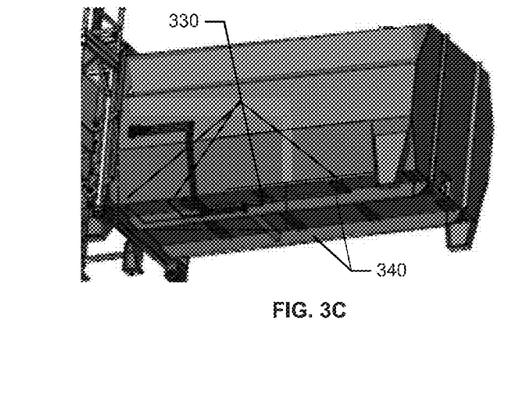

FIGS. 3A-3C show another exemplary waste treatment system 300, which is similar to system 100. In addition to hopper 110, shredder 120, lateral waste transporter 130, roll-off treatment bin 140, control module 150, and ozone module 160, system 300 includes a cart loader system 310, self-sealing opening (or front bin diaphragm) 321, ozone injectors 330, and roll-off guide rails 340.

Cart loader system 310 includes a cart receiving area 311, a cart holder 312, a waste cart 313, and a cane dumper 314. Cart receiving area 311 provides a gated fenced area around cart holder 312, waste cart 313, and cane dumper 314. Cart holder 312 includes a front gate which opens to allow a worker insert waste cart 313 into the holder. Waste cart 313 includes one or bags 315 of biomedical and/or pharmaceutical waste. Cane dumper 314, which may take a variety of forms, such as hydraulic or electric, engages with cart holder 312, lifting and angularly rotating it (through an inverted J or cane path) from a first position P1 to a second, higher position P2. In the second position, an extended angled portion of cart holder 312 aligns with an opening of hopper 110, and bags 315 fall under force of gravity out of waste cart 313 into the hopper and onto shredder 120 for resizing or shredding. The shredded waste exits into lateral transporter 130 (for example an auger compactor) which conveys it into treatment bin 140.

FIG. 3B shows a front wall 320 of treatment bin 140, with the wall including self-sealing opening 321. Opening 321 receives a right cylindrical extension nozzle portion (not shown) of lateral transporter 130. Self-sealing opening 321 includes an elastic sealing disk which covers a circular opening in the front wall (wall closest to the lateral transporter) of treatment bin 140. The extension nozzle can be pushed into the self-sealing opening, bending and stretching radial fin portions of the sealing disk inward and creating an effective seal around the nozzle. When the bin is pulled away from the lateral conveyer the extension nozzle slides out of opening 321 and the opening closes due to its inherent resiliency, thereby reducing or completing eliminating any spillage. (See U.S. Published Patent Application US 2012/0060705A1, which was published on Mar. 15, 2012 and which is incorporated herein by reference, for further details.)

FIG. 3C further shows that in system 300, treatment bin 140 includes eight ozone injectors 330 which are arranged in two rows of four along the bottom of bin 140. Also shown is a pair of roll-off guide rails 340, which engage with roll-off guides on a flat-bed truck to facilitate loading and unloading of the bin. Bin 140 also includes an exhaust manifold (not shown), for example, an elongated perforated tube, that extends lengthwise and adjacent to a ceiling of treatment bin 140.

Exemplary Method(s)

Figure 4:
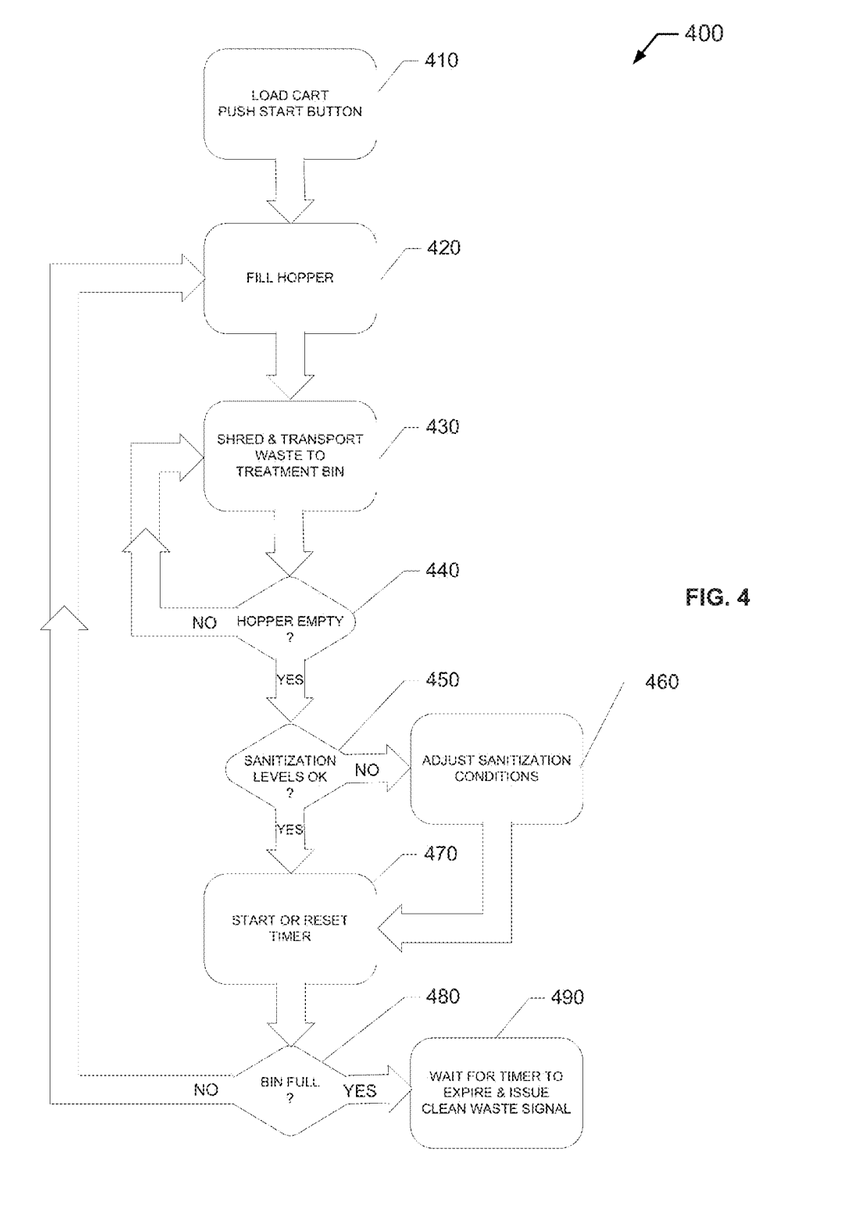
FIG. 4 is a flow chart of an exemplary method of operating a waste treatment system, such as system 100 and/or system 300, and which corresponds to one or more embodiments of the present invention.

FIG. 4 shows a flow chart 400 of an exemplary method of operating a biomedical waste treatment system, such as system 100 or system 300. Flow chart 400 includes process blocks 410-490.

In block 410, the exemplary process begins with system initialization. In the exemplary embodiment, this entails a user actuating a start button or switch and the system responsively starts the shredder and lateral transporter and begins establishing sanitization conditions, for example desired ozone concentration and humidity levels, within treatment bin 140. In some embodiments, a cart of medical waste is loaded onto or otherwise mechanically coupled onto a lift mechanism, such as a cane dumper, and weighs the cart to determine the quantity of medical waste. Execution then continues at block 420.

Block 420 entails filling the hopper with medical waste from a waste cart, such as waste cart 313 in FIG. 3A. In the exemplary embodiment, this entails lifting and dumping contents of the medical waste cart into hopper 110. The dumped cart is then lowered, enabling a user or autocart loading system to load another cart into cart holder 312. In the exemplary embodiment, the cane dumper includes a scale, enabling weighing and recording of the weight of the waste in waste cart 313 as well as calculating the cumulative weight of waste provided to bin 140. Execution continues at block 430.

Block 430 entails shredding and transporting medical waste into the treatment bin. In the exemplary embodiment this entails shredding waste as it drops through hopper 110 onto the blades of shredder 120. It also entails monitoring electrical parameters associated with the shredder and/or transporter to determine its operational status as normal operation, overloaded, or partially loaded, or jammed.

Block 440 entails determining whether the hopper is empty or not, or more generally whether there is additional waste ready for processing. To this end, the exemplary system, or more precisely controller or processor, uses the electrical load status of the shredder as a proxy or indicator for whether the shredder is actually shredding. (Since the hopper has an open bottom in the exemplary embodiment, the load status of the shredder is also indicative of hopper-fill status.) For example, if the electrical current, measured in amperes, drawn by the shredder is less than a threshold amount, the system deems that the hopper is empty or nearly empty, and if the current is greater than the threshold amount, the hopper is deemed "not empty." If the hopper is deemed not empty, execution branches back to block 430 for continued shredding and transporting of waste into treatment bin 140 (FIG. 1). However, if the hopper is deemed to be empty, execution continues at block 450.

Block 450 entails determining whether the sanitization levels within treatment bin are acceptable. In the exemplary embodiment, this entails determining ozone and humidity levels within the treatment bin and comparing them to established thresholds. (In some embodiments, the thresholds levels are a function of waste type and/or waste density as determined using the weight of a cart load of the waste and/or electrical load drawn by the shredder.) Exemplary ozone levels include 1000, 2000, 3000, . . . , 20,000 parts per million (ppm), and exemplary humidity levels include 10, 20, 30, . . . , 100 percent. Some embodiments also control temperature within the treatment bin to promote optimal sanitization. If sanitization conditions are deemed unacceptable, executions branches to block 460, which entails adjusting the conditions by for example injecting ozone and/or water vapor to acceptable levels. And, if they are deemed acceptable, execution continues at block 470.

Block 470 entails starting or resetting a treatment timer. In the exemplary embodiment, this entails resetting an X-minute countdown or countup timer, where X is selected from a range of 1-999 minutes, for example 5, 10, 15, 20, . . . , 100 minutes. The exemplary timer may be implemented in software or via dedicated analog or digital circuitry. Execution continues at block 480.

In block 480, the system determines whether the treatment bin is full or not. In the exemplary embodiment, this determination is based on cumulative weight of waste loaded into the bin (since emptied last) relative to a maximum rated weight for the treatment bin. If the system deems that the treatment bin is not full, execution branches back to block 410, to await loading of another cart of waste. If the system deems that the bin is full, for example by virtue of its cumulative waste weight being less than an average cart's weight from the maximum rated weight, execution continues at block 490.

Block 490 entails waiting for the treatment timer to expire and issuing a clean-waste (or ready-to-transport) signal. In the exemplary embodiment, this entails continued monitoring of the sanitization condition within the treatment bin, and resetting the timer (back to zero if a countup timer or back to its end time if a countdown timer) if measured conditions in the treatment bin do not comply with the desired sanitization conditions. In some embodiments, the system determines cumulative time that the bin complies with the desired sanitization conditions, or cumulative time since the last bin-full condition that the bin was non-compliant, adjusting the timer to the minimum amount necessary to ensure exposure of the waste to desired sanitization conditions for the desired time. In the exemplary embodiment, issuance of the clean-waste signal causes the system to evacuate residual ozone from the treatment bin through an ozone destruct system to the atmosphere and to allow decoupling of the treatment bin from the lateral waste transporter. Some embodiments may also activate visual indicators on the treatment bin, such as LED lights, to indicate that the waste has been sanitized.

Conclusion

In the foregoing specification, specific embodiments have been described. However, one of ordinary skill in the art appreciates that various modifications and changes can be made without departing from the scope of the invention as set forth in the claims below. Accordingly, the specification and figures are to be regarded as illustrative rather than restrictive, and all such modifications are included within the scope of present teachings.

The benefits, advantages, solutions to problems, and any element(s) that may cause any benefit, advantage, or solution to occur or become more pronounced are not to be construed as critical, required, or essential features or elements of any or all the claims. The invention is defined solely by the appended claims including any amendments made during the pendency of this application and all equivalents of those claims as issued.

It will be appreciated that some embodiments may comprise one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, some embodiments or portions thereof can be implemented as a computer-readable volatile and/or non-volatile storage medium or memory (more generally a non-transitory machine-readable storage medium) having computer readable code or instructions stored thereon for directing operation of or causing programming of a computer (e.g., including one or more processors) to perform one or more portions of method as described and/or claimed herein. Exemplary computer-readable storage mediums include a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory.

The Abstract of the Disclosure is provided to allow the reader to quickly ascertain the nature of the technical disclosure. It is submitted with the understanding and intent that it not be used to interpret or limit the scope or meaning of the claims. In addition, in the foregoing Detailed Description, various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A biomedical waste treatment assembly comprising:
container means, having a nominal capacity of at least 10 cubic yards and an
exterior surface at least partially defined by a bottom, a top, and a sidewall, for containing shredded biomedical waste received through an opening in the exterior surface, with the opening including an elastic sealing disk assembly;
a set of one or more ozone injectors mounted to the container means;
a set of one or more ozone sensor probes mounted directly to the exterior surface of the container means;
at least one wheel for enabling rolling of the container means; and
at least one guide rail to engage with a corresponding guide portion of a truck.

2. The assembly of claim 1, wherein the one or more ozone injectors are mounted on the bottom or top of the container means.

3. The assembly of claim 1, further including one or more ozone conduits for connection to an ozone generator, with the conduits mounted to the bottom and the sidewall of the container means and in fluid communication with the one or more ozone injectors.

4. The assembly of claim 1, further comprising:
an ozone destructor in fluid communication with an interior volume of the container means.

5. The assembly of claim 1, further comprising:
a shredder positioned outside the container means and configured to produce the shredded biomedical waste; and
means, responsive to an operating condition of the shredder, for starting measurement of treatment time for the shredded biomedical waste within the container means.

6. The assembly of claim 1:
wherein the ozone injectors are in fluid communication with means for generating humidified ozone.

7. A biomedical waste treatment assembly comprising:
container means, including an interior volume and a surface, for containing shredded biomedical waste received through a self-sealing opening in the surface;
injector means, at least partially mounted to the surface of the container means, for injecting humidified ozone into the interior volume of the container means;
one or more ozone sensor probes mounted to the surface of the container means for sensing ozone within the interior volume; and
one or more roll-off guide rails mounted to the surface of the container means for engaging with a corresponding guide portion of a truck.

8. The assembly of claim 7, further comprising
a shredder for providing the shredded biomedical waste; and
means, responsive to an operating condition of the shredder, for controlling measurement of treatment time for shredded biomedical waste within the container.

9. The assembly of claim 7, wherein the means for controlling measurement of treatment time includes a processor or a programmable logic controller coupled to a shredder current sensor.

10. The assembly of claim 8, further comprising:
a lateral conveyor positioned below the shredder to receive and convey the shredded biomedical waste into the container means through the self-sealing opening.

11. The assembly of claim 7, wherein the container means includes first and second loads of shredded biomedical waste, with the first load having been exposed to ozone in the container means for a first time period and the second load exposed to ozone in the container means for a second time period that includes the first time period.

12. A biomedical waste treatment assembly comprising:
roll-off container means, including an interior volume and an exterior surface, for containing shredded biomedical waste received through a self-sealing elastic opening in the surface;
one or more fluid conduits for fluid communication with and connection to means for generating humidified ozone that is positioned outside the container means, each conduit mounted outside the interior volume to the exterior surface of the container means; and
injection means, in fluid communication with one or more of the fluid conduits, for injecting humidified ozone into the interior volume of the container means; and
one or more ozone sensor probes mounted to the surface of the container means for sensing ozone within the interior volume.

13. The assembly of claim 12, further comprising
a shredder for providing the shredded biomedical waste; and
means, responsive to an operating condition of the shredder, for controlling measurement of treatment time for shredded biomedical waste within the container.

14. The assembly of claim 13, wherein the means for controlling measurement of treatment time includes a processor or a programmable logic controller coupled to a shredder current sensor.

15. The assembly of claim 12, further comprising first and second guide rails mounted to a bottom surface of the container means, with one or more of the conduits mounted between the first and second guide rails.

16. A biomedical waste treatment assembly comprising:
roll-off container means, including an exterior surface and having a nominal capacity of at least 10 cubic yards, for containing shredded biomedical waste received through a self-sealing elastic opening in the exterior surface and for selective engagement and disengagement with a roll-off truck;
one or more ozone sensor probes mounted to the exterior surface of the container means; and
an ozone destructor in fluid communication with an interior volume of the container means.

17. The assembly of claim 16, further comprising:
one or more conduits for connection to means for generating humidified ozone, each conduit mounted to the surface of the container means; and
injection means, in fluid communication with one or more of the conduits, for injecting humidified ozone into the interior volume of the container means, with the humidified ozone having a relative humidity of at least 70 percent.

18. The assembly of claim 17,
wherein the container means further includes:
at least one wheel to enable rolling of the container means; and
at least one guide rail to engage with a corresponding guide portion of a truck.

19. The assembly of claim 18, further comprising
a shredder for providing the shredded biomedical waste; and
means, responsive to an operating condition of the shredder, for controlling measurement of treatment time for shredded biomedical waste within the container means.

* * * * *